United States Patent [19]

Lewin

[11] 4,138,288
[45] * Feb. 6, 1979

[54] METHOD AND APPARATUS FOR OXYGENATING AND REGULATING THE TEMPERATURE OF BLOOD

[75] Inventor: John E. Lewin, Santa Ana, Calif.

[73] Assignee: Shiley Scientific Incorporated, Irvine, Calif.

[*] Notice: The portion of the term of this patent subsequent to Dec. 27, 1994, has been disclaimed.

[21] Appl. No.: 863,989

[22] Filed: Dec. 23, 1977

Related U.S. Application Data

[63] Continuation-in-part of Ser. No. 685,020, May 10, 1976, Pat. No. 4,066,264.

[51] Int. Cl.² .............................................. A61M 1/03
[52] U.S. Cl. ............................... 195/1.8; 128/DIG. 3; 165/1; 165/163; 165/184; 422/46; 422/47; 424/101
[58] Field of Search ................ 23/258.5 R, 258.5 BH, 23/258.5 MH, 258.5 A, 258.5 B; 165/1, 163, 184; 128/399, 400, DIG. 3; 195/1.8

[56] References Cited

U.S. PATENT DOCUMENTS

| | | | |
|---|---|---|---|
| 2,374,609 | 4/1945 | McCollum | 165/184 X |
| 2,934,067 | 4/1960 | Calvin | 23/258.5 BH |
| 3,015,355 | 1/1962 | Humphrey | 29/423 X |
| 3,291,568 | 2/1966 | Sautter | 23/258.5 BH |
| 3,437,450 | 4/1969 | Greenwood | 23/258.5 A |
| 3,468,631 | 9/1969 | Raible et al. | 23/258.5 BH |
| 3,578,411 | 5/1971 | Bentley et al. | 23/258.5 BH |
| 3,730,229 | 5/1973 | D'Onofrio | 165/184 X |
| 3,746,084 | 7/1973 | Ostbo | 165/163 |
| 3,769,162 | 10/1973 | Brumfield | 23/258.5 BH |
| 3,802,499 | 4/1974 | Garcea | 165/163 |
| 3,898,045 | 8/1975 | Bowley | 23/258.5 BH |
| 4,065,264 | 12/1977 | Lewin | 23/258.5 BH |
| 4,067,696 | 1/1978 | Curtis | 23/258.5 B |

FOREIGN PATENT DOCUMENTS 1144448  3/1969  United Kingdom .................... 165/184

Primary Examiner—Barry S. Richman
Attorney, Agent, or Firm—Knobbe, Martens, Olson, Hubbard & Bear

[57] ABSTRACT

A blood oxygenator includes a heat exchanger wherein heat transfer fluid flows through a tube which is ribbed along its length. The tube is positioned within a chamber connected in an extracorporeal blood circuit such that the blood is caused to flow over the exterior surface of the ribbed tube. In the preferred embodiment, the blood flows through a plurality of continuous, restricted area flow paths offering substantially uniform flow impedance to the blood, these restricted flow paths being provided by constructing the tube with an integral, substantially continuous, hollow, helical rib, and by forming the helically ribbed tube in a helical configuration mounted between an inner cylindrical column and an outer cylindrical shell such that the blood is caused to flow through the plural paths of restricted cross-sectional area provided by the helical flute. In one embodiment, the heat exchanger tube and blood chamber are formed as an independent unit adapted for use in the desired location of an extracorporeal blood circuit. In the other embodiments, the heat exchanger is formed integral with a blood oxygenator in which oxygen is absorbed into the blood and carbon dioxide is released therefrom. In the preferred embodiment, the heat exchanger also performs substantially all of the transfer of oxygen into the blood and the removal of carbon dioxide from the blood.

24 Claims, 16 Drawing Figures

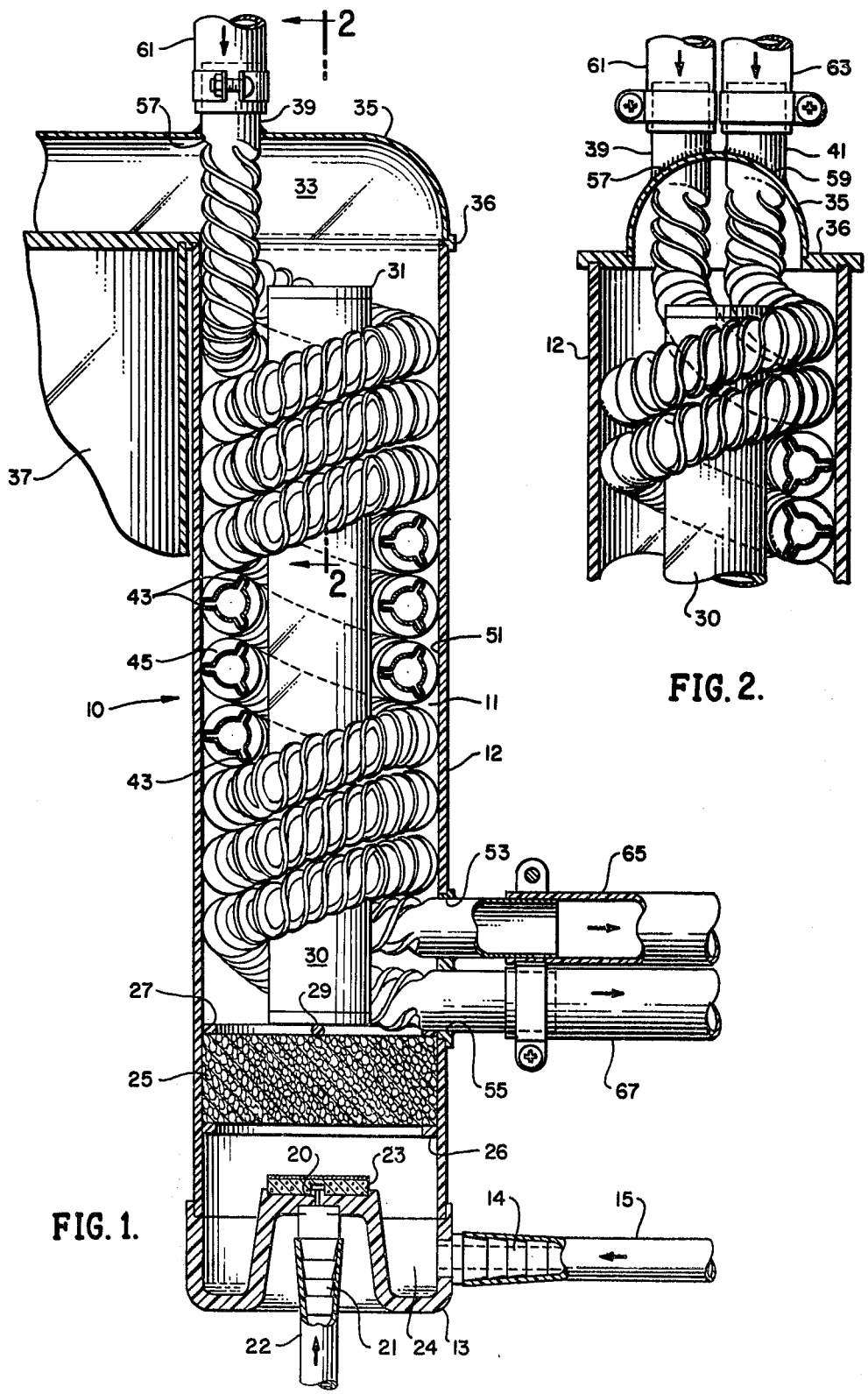

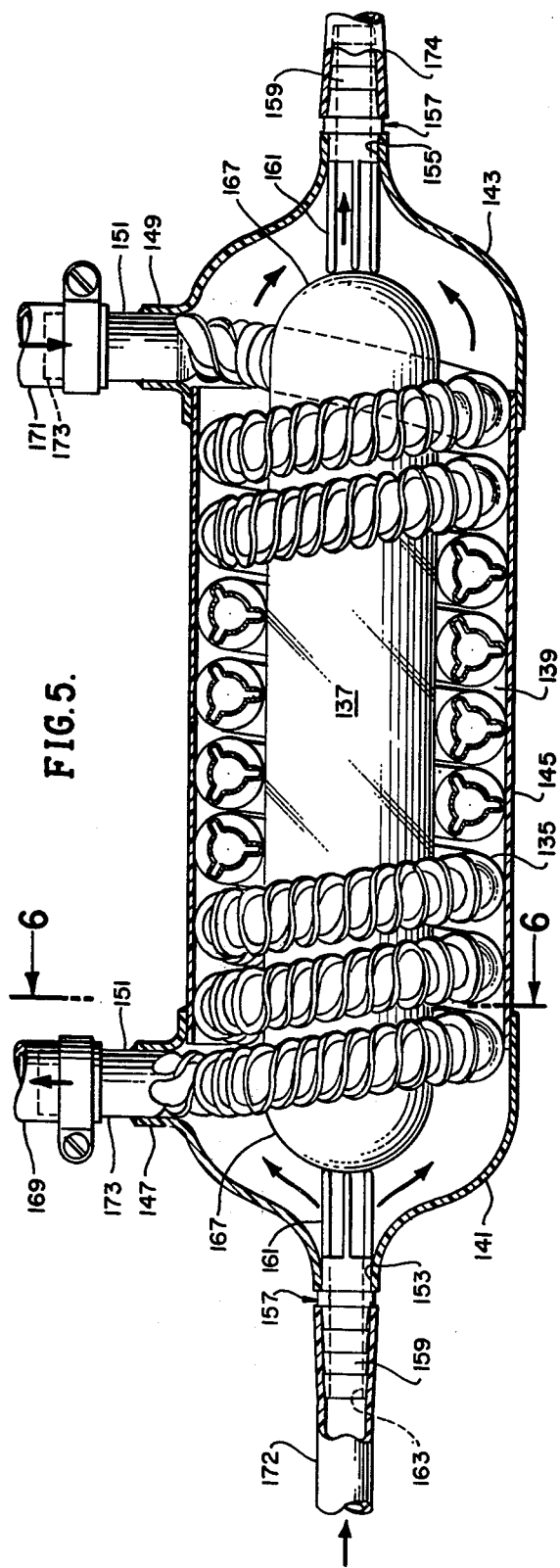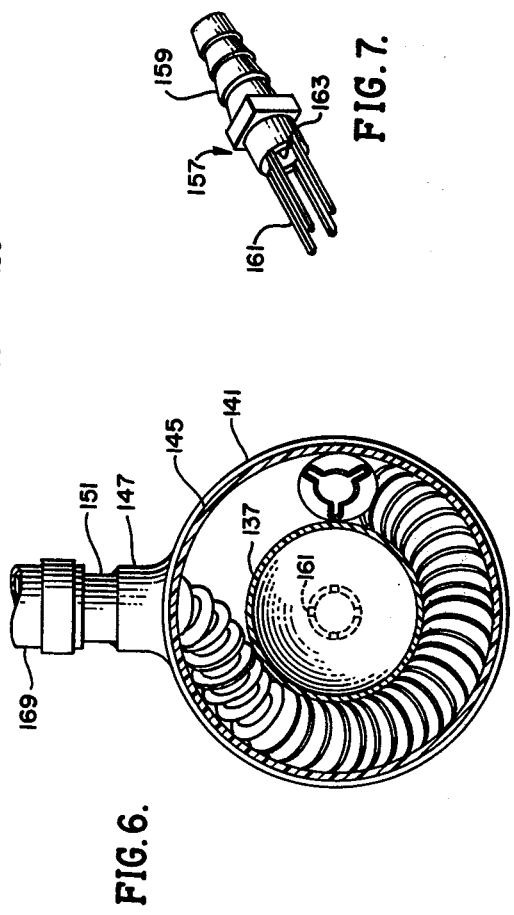

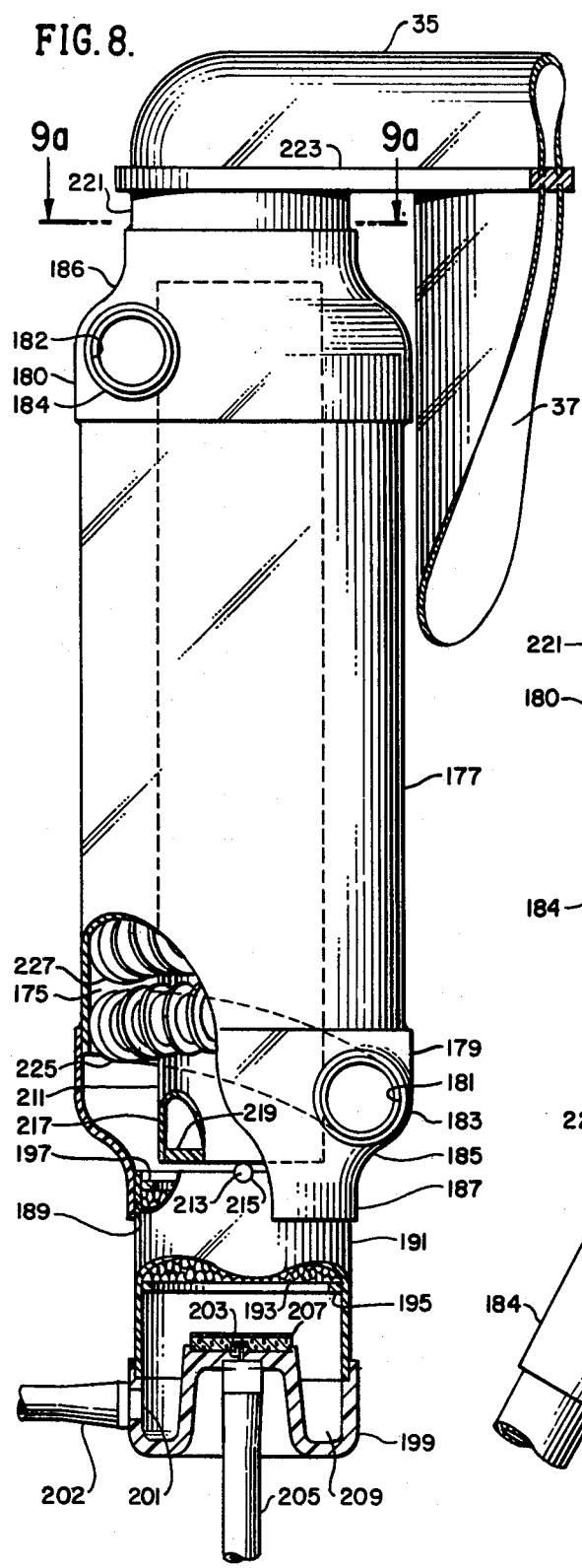
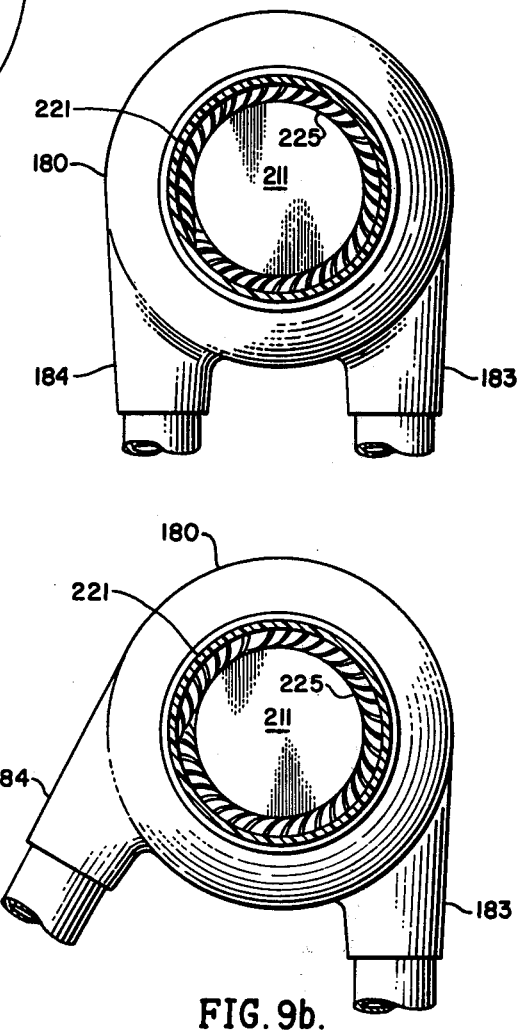
FIG. 8.
FIG. 9a.
FIG. 9b.

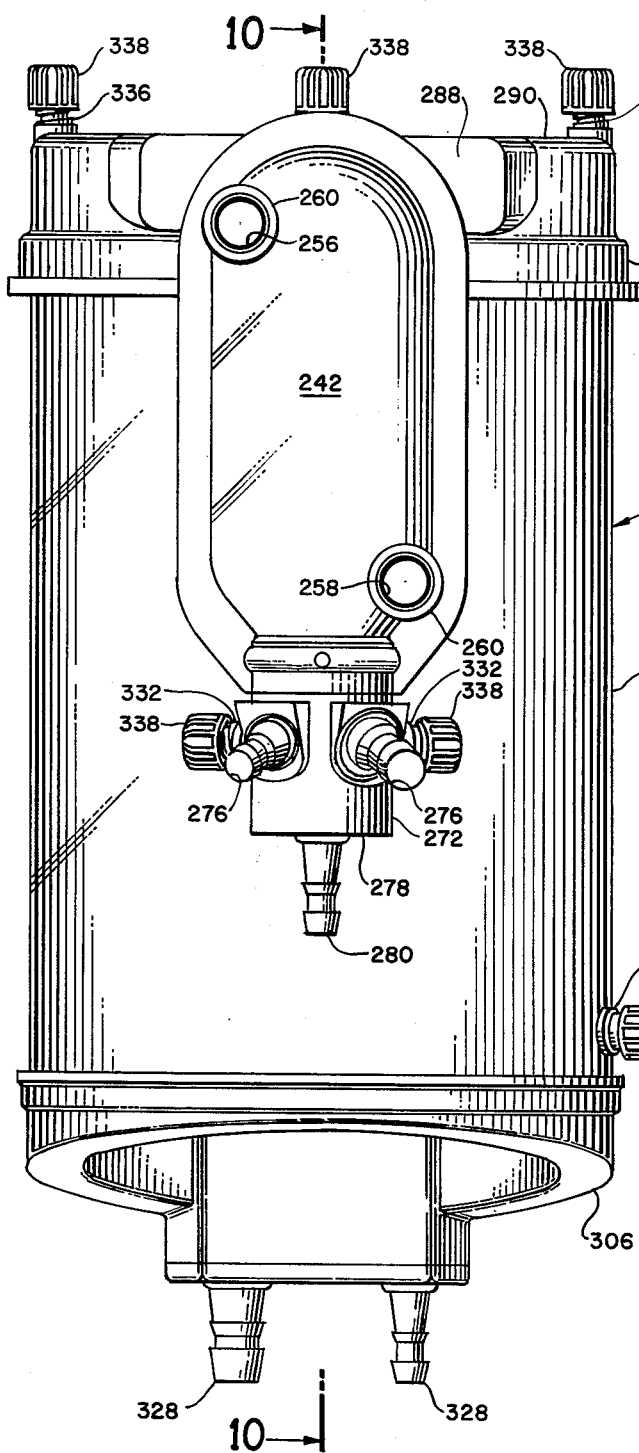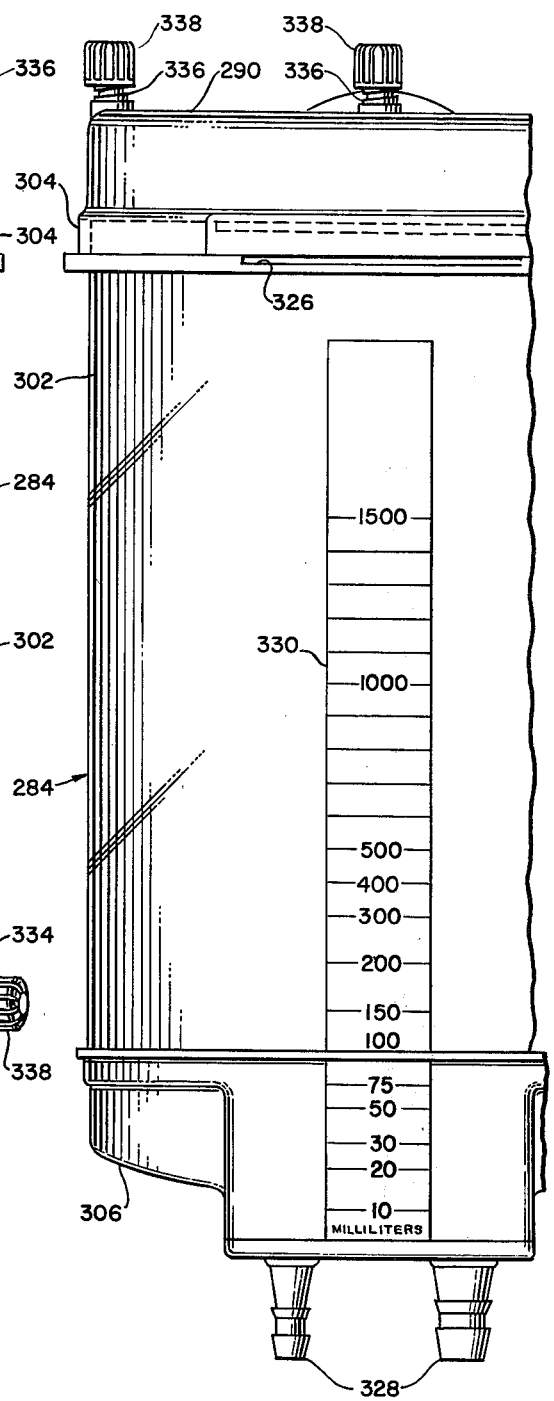
FIG. 11.                    FIG. 12.

METHOD AND APPARATUS FOR OXYGENATING AND REGULATING THE TEMPERATURE OF BLOOD

CROSS-REFERENCE TO RELATED APPLICATION

This is a Continuation-In-Part of co-pending application Ser. No. 685,020, filed May 10, 1976, now U.S. Pat. No. 4,065,264 issued December 27, 1977

BACKGROUND OF THE INVENTION

Extracorporeal circulation is and has been a routine procedure in the operating room for several years. An important component in the extracorporeal blood circuit is a heat exchanger used to lower the temperature of the blood prior to and during a surgical procedure and subsequently rewarm the blood to normal body temperature. The cooled blood induces a hypothermia which substantially reduces the oxygen consumption of the patient. The published literature indicates that the oxygen demand of the patient is decreased to about one-half at 30° C., one-third at 25° C. and one-fifth at 20° C. Light (33 to 35° C), moderate (26 to 35° C), and deep (20° and below) hypothermia are commonly used in clinical practice. Hypothermia is used to protect the vital organs including the kidneys, heart, brain and liver during operative procedures which require interrupting or decreasing the perfusion.

A number of different structural configurations for heat exchangers have been used in the extracorporeal blood circuit including hollow metals coils, cylinders and plates through which a heat transfer fluid (typically water) is circulated. A survey of a number of different types of heat exchangers used in extracorporeal circulation is included in the book entitled "Heart-Lung Bypass" by Pierre M. Galletti, M.D. et al, pages 165 to 170.

Notwithstanding the plurality of different types of heat exchanger configurations which have been used in the past, there remains a need for a safe highly efficient heat exchanger design which is simple to use and yet inexpensive enough to be manufactured as a disposable item. Thus, it is important that there not be any leakage of the heat transfer fluid into the blood. This fluid is typically circulating water flowing from plumbing fixtures located in the operating room. Certain of the heat exchangers commonly used today for clinical bypass operations have an upper pressure limit which is sometimes lower than the water pressures obtainable in the hospital operating room. The person who connects up the heat exchanger must therefore be very careful to never apply the full force of the water pressure through such a heat exchanger. Failing to take this precaution, or an unexpected increase in water pressure, could cause a rupture within the heat exchanger resulting in contamination of the blood flowing through the blood oxygenator.

It is also important that the heat exchanger have a high performance factor in order to reduce to a minimum the time required to lower the temperature to induce hypothermia and subsequently raise the blood temperature to normal. Some physiological degradation of the blood occurs after a patient is connected only a few hours to any of the bubble oxygenators presently in use. Therefore, time saved in cooling and rewarming the blood is of direct benefit to the patient and also gives the surgeon additional time to conduct the surgical procedure if necessary.

SUMMARY OF THE INVENTION

The present invention relates to a heat exchanger for an extracorporeal blood circuit formed by a metal tube having integral, hollow ribbing along its length. This tube in turn is formed in an overall helical configuration and mounted between an inner cylindrical column extending within the helically configured tube and an outer cylindrical shell. Both the column and the shell are sized such that peripheral portions of the ribbing are in contact with or are closely proximate to the exterior wall of the column and the interior wall of the cylindrical shell. The method employed for regulating the temperature of blood using this type of heat exchange element involves flowing a heat transfer fluid through the tube and hollow rib and flowing the blood in a counterflow direction over the exterior surface of the ribbed tube. The combination of the rib and the contacting surfaces of the cylinder and chamber confine the flow of blood surstantially within paths of restricted area and extended length provided by the ribbing.

The heat exchanger of the present invention enjoys several significant advantages. Thus, its performance factor is very high due to the long residence time of the blood, the high conductivity of the heat exchange tube, the counterflow operation, and high flow rate of the heat transfer fluid through the ribbed tube.

Heat exchangers constructed in accordance with the present invention have the reliability necessary for routine use in open heart surgery and other procedures utilizing extracorporeal circulation. The metal heat transfer fluid tube is an integral member which may be completely tested, both before and after assembly into the blood chamber, for leaks under substantially higher fluid pressures than are ever encountered in an operating room environment. The integral nature of the heat exchange tube also provides an important advantage in that only the ends of the tube pass throug the wall of the blood carrying chamber, thus minimizing the number of openings in the chamber which must be hermetically sealed. Moreover, no connections need to be made to the tube within the blood chamber since a heat transfer fluid inlet and heat transfer fluid outlet are provided by the ends of the tube extending out from the chamber. Any leak at the connection of the heat exchanger tube and the fluid supply conduit will merely leak water or other heat transfer fluid external of the blood chamber.

The ribbed heat exchanger tube may be mounted within a blood chamber separate from the blood oxygenator or may be incorporated integral with the blood oxygenator, e.g., in the venous side within the blood-oxygen mixing chamber or in the outlet side within the defoaming chamber. In the embodiments described below in which the heat exchanger is incorporated within the mixing chamber of a bubble oxygenator the flow of the blood and blood foam through the lengthy paths of restricted cross-sectional area contributes to the blood-gas transfer process, and, in one embodiment, this flow of blood and blood foam effects substantially all of the blood-gas transfer process.

The heat exchangers of this invention are sufficiently economical in terms of material and manufacturing costs so that it is disposed of after use, thus avoiding the problems and cost of sterilization in the hospital. In addition, the heat exchangers constructed in accordance with this invention may be made biologically inactive and compatible with human blood.

BRIEF DESCRIPTION OF THE DRAWINGS

FIG. 1 is a vertical elevational partial sectional view of a blood oxygenator having an integral heat exchanger constructed in accordance with the present invention;

FIG. 2 is a partially sectional view taken along the line 2—2 of FIG. 1;

FIG. 5 is a vertical elevational partially sectional view of a heat exchanger constructed in accordance with the present invention for use as a separate component in an extracorporeal blood circuit;

FIG. 6 is a partially sectional view taken along the line 6—6 of FIG. 5;

FIG. 7 is a perspective view of the port member providing a fluid conduit, a ridged connector and rods for positioning the centrally located column shown in FIG. 5;

FIG. 8 is a vertical elevational partial sectional view of another embodiment of a blood oxygenator having an integral heat exchanger constructed in accordance with the present invention;

FIG. 9a is a partially sectional view taken along the line 9—9 of FIG. 8 showing the heat exchanger tube ends in parallel alignment;

FIG. 9b is a partially sectional view taken along the line 9—9 of FIG. 8 showing the heat exchanger tube ends in a non-parallel alignment;

FIG. 11 is a front elevational view of the preferred embodiment of the present invention;

FIG. 12 is a fragmentary rear elevational view of the defoamer section of the preferred embodiment of a blood oxygenator having an integral heat exchanger constructed in accordance with the present invention;

Figure 3:
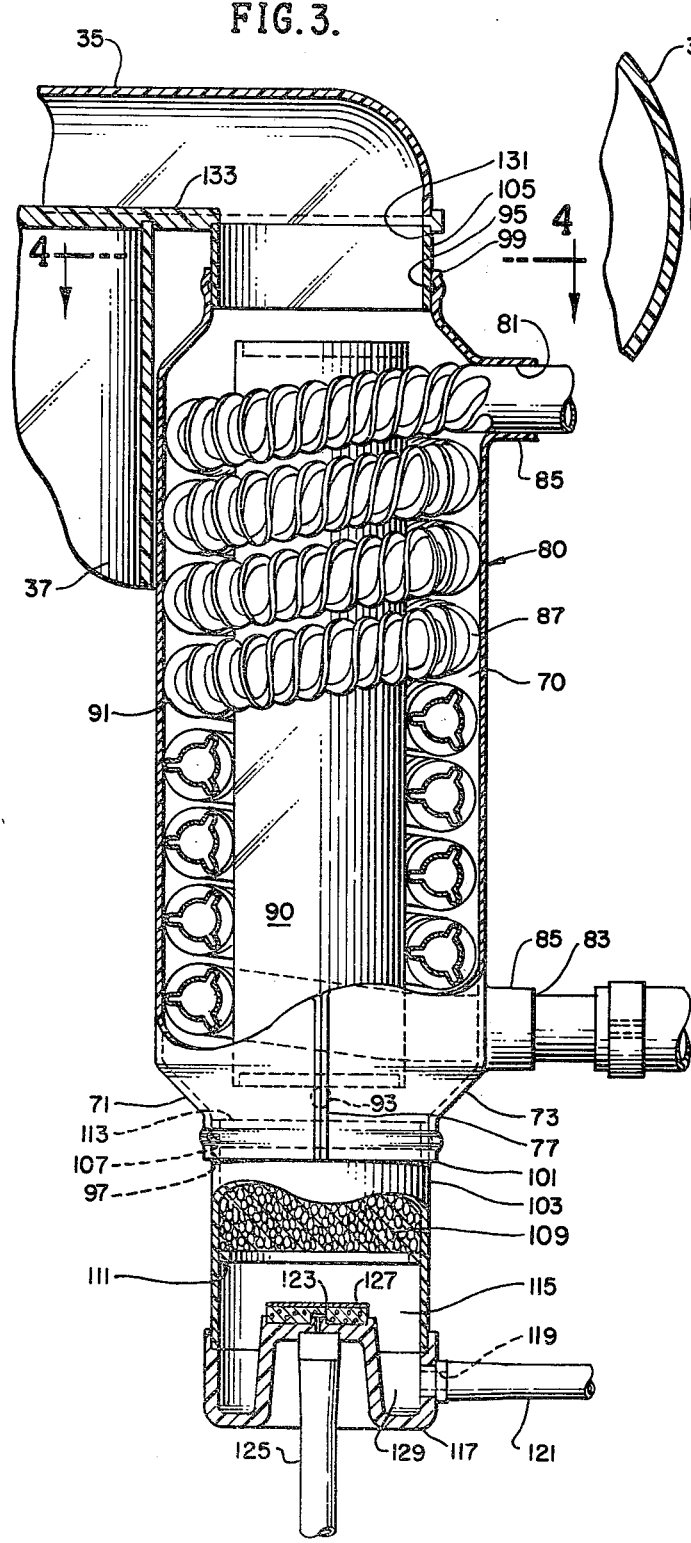
FIG. 3 is a vertical elevational partial sectional view of another embodiment of a blood oxygenator having an integral heat exchanger constructed in accordance with the present invention.

DETAILED DESCRIPTION OF THE EMBODIMENT OF FIGS. 1 and 2

Referred to FIGS. 1 and 2, a blood oxygenator 10 is shown incorporating a heat exchanger in accordance with this invention. In this first embodiment as well as the other embodiments described below and illustrated in FIGS. 3, 4, 8, 9a and 9b, the blood oxygenator 10 is shown constructed in accordance with the invention disclosed and claimed in application Ser. No. 655,039, filed Feb. 3, 1976 by Robert M. Curtis, entitled BLOOD OXYGENATOR, Now U.S. Pat. No. 4,067,696 issued Jan. 10, 1978, and assigned to Shiley Laboratories, Inc., the assignee of the present invention. The bubble oxygenator chamber 11 is formed by a cylindrical shell 12 having its lower end closed off by a multi-port end cap 13. In the outer wall of the end cap 13 are formed one or more blood inlet ports, one such port 14 being connected to the extracorporeal blood circuit by a flexible venous blood conduit 15. In the center of the cap 13 and extending through the wall thereof is an oxygen inlet port 20 including an outwardly extending ridged connector 21 for attachment to a flexible oxygen line 22. The oxygen entering the inlet port 20 is caused to form a plurality of oxygen bubbles by means of sparger 23. These bubbles flow through the venous blood entering the annular trough 24 formed by the end cap 13 and the blood and oxygen mixture flow upwardly through a three-dimensional, open cellular mixing material 25 supported above the sparger 23 within the chamber 11 by a pair of annular retaining rings 26 and 27. The mixing material 25 is formed as a cylinder so as to completely fill the cross-sectional space within the cylindrical shell 12 between the annular retaining rings 26 and 27. A A column 30 is coaxially mounted within the upright cylindrical shell 12 and supported by a horizontal rod 29 formed as an integral cross brace of the annular retaining ring 27. Both ends of the column 30 are hermetically sealed by caps 31.

The top of the chamber 11 is open. The arterialized blood in the form of liquid blood and blood foam rises through this opening and is contained in a channel 33 formed by a generally half cylindrical shell 35 secured to a flat cover plate 36. As described in the co-pending application of Robert M. Curtis, supra, the channel 33 leads to a defoamer chamber 37 wherein the foam is collapsed and the arterialized whole blood collected and returned to the extracorporeal blood circuits.

The heat exchanger comprises a pair of helically ribbed, heat transfer fluid tubes 39 and 41. As shown, the hollow ribs 43 on these tubes have a triple helix configuration and provided a continuous series of helical flutes 45. These helically ribbed tubes 39 and 41 are advantageously constructed from a thin wall tube of metal. Methods and apparatus for manufacturing such helically ribbed tubes are described in U.S. Pat. Nos. RE24,783 and 3,015,355.

An aluminum tube so formed and subsequently externally coated with a thin coating of polyurethane provides a relatively inexpensive, reliable and highly efficient heat exchanger element. The polyurethane film coating enables compatibility with human blood, this coating being advantageously applied electrolytically as a powder and subsequently heated to provide a very permanent coating over the exterior surface of the aluminum tube. Stainless steel may also be used and has the advantage of not requiring any coating for blood compatibility but also has certain inherent disadvantages. Thus, this metal is a substantially poor conductor of heat and is appreciably more expensive than aluminum.

As shown in FIG. 1 and 2, the helically ribbed tubes 39 and 41 are formed in a helical configuration and mounted between the central column 30 and the interior wall of the shell 12 such that peripheral portions of the ribs are closely proximate to and advantageously in contact with the exterior surface of the column 30 and the interior wall 51 of the bubble oxygen chamber 11. One end of each of the respective tubes 39 and 41 passes through hermetically sealed openings 53 and 55 formed in the bottom of the chamber 11 and the opposite ends of the tubes extend through hermetically sealed openings 57 and 59 formed in the cylindrical shell 35. Urethane glue provides and effective sealant between the outer surface of the polyurethane coated tube and the chamber 11 and shell 35 formed of polycarbonate plastic.

Shell 12 is advantageously extruded from polycarbonate plastic and includes a longitudinal slit (not shown) such that the shell may be opened up during manufacture to accept the helically ribbed tubes 39 and 41. After these tubes and the inner column 30 are mounted in place, the slit edges of the shell are bonded together by ethylene dichloride.

Flexible conduits 61 and 63 are clamped to the upper ends of tubes 39 and 41 for supplying a heat transfer fluid, typically water under pressure, at the desired temperature. The lower ends of the ribbed tubes 39 and 41 are connected through flexible conduits 65 and 67 to a drain. In this manner, the flow of heat transfer fluid is opposite to that of the flow of the blood in the oxygenator chamber 11 to produce a counterflow-type heat exchanger.

Since the embodiment of FIGS. 1 and 2 has many features and advantages in common with the other embodiments described below, such features and advantages are described in detail hereinafter. A primary distinguishing feature of the embodiment of FIGS. 1 and 2 is the use of the dual heat exchanger tubes 39 and 41. The heat transfer performance of a heat exchanger is related to the flow rate of the heat transfer fluid. Although the single tube heat exchanger shown in the embodiments described hereinafter has been found to have a most satisfactory performance in all operating room environments tested to date, the double tube embodiment of FIGS. 1 and 2 would be particularly useful if only very low flow rates of heat transfer fluid were available during the extracorporeal procedure.

Figure 4:
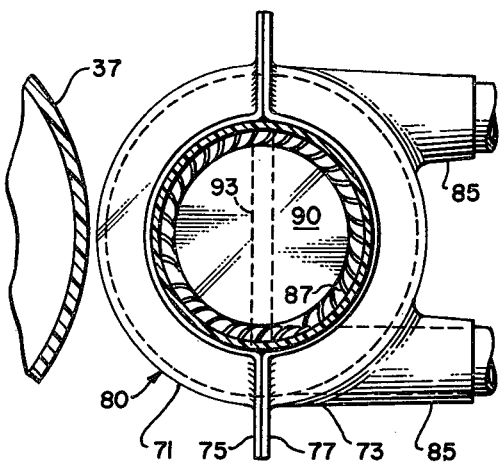
FIG. 4 is a partially sectional view taken along the line 4—4 of FIG. 3.
Figure 10:
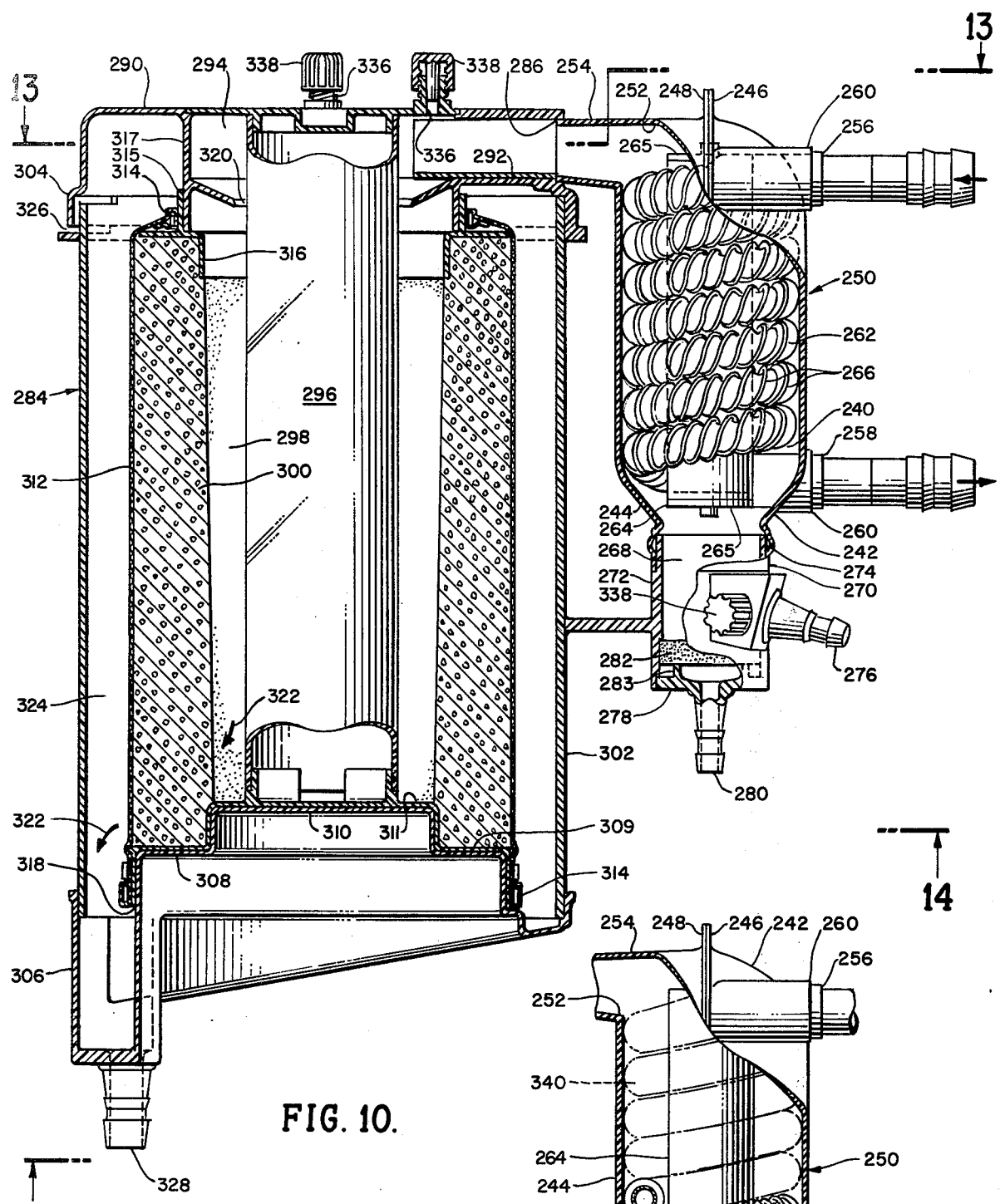
FIG. 10 is a vertical elevational sectional view along the line 10—10 of FIG. 11 of the preferred embodiment of a blood oxygenator having an internal heat exchanger constructed in accordance with the present invention.

DETAILED DESCRIPTION OF THE EMBODIMENT OF FIGS. 3 and 4

Another embodiment of a blood oxygenator incorporating an integral heat exchanger in accordance with this invention is shown in FIGS. 3 and 4. In this embodiment, the bubble oxygenating chamber 70 is formed by a pair of mating plastic shells 71 and 73, each including a flat peripheral flange 75 and 77 which may be joined together to form a complete cylindrical shell 80. Shell halves 71 and 73 are advantageously formed by vacuum forming or injection molding polycarbonate plastic.

Cylindrical shell 80 includes an upper side opening 81 and a lower side opening 83 each having an integral outwardly extending cylindrical boss 85 through which extends the respective ends of a single helically ribbed heat transfer fluid tube 87. The inside wall of these extending cylindrical bosses 85 and the proximate exterior surface of the heat exchanger tube 87 are bonded together to effect a hermetic seal. Ethylene dichloride forms an excellent bond between shell halves formed of polycarbonate plastic.

A particular advantage of the construction shown in FIGS. 3 and 4 is that the heating coil 87 may be easily assembled within the chamber 70. When the ribbed tube 87 is formed into a helical configuration, it has a tendency to open up, thereby resulting in a certain amount of sliding frictional contact with the inside walls of the chamber 70 and the exterior walls of the column 90 when mounted in a unitary cylindrical shell such as shown in FIGS. 1 and 2 at 12. In the embodiment of FIGS. 3 and 4, the interior column 90 is inserted within the helically formed ribbed tube 87 and both members placed in the shell half 73 such that the two ends of heat exchange tube 87 extend through the openings 81 and 83. The mating shell half 71 is placed over the heat exchanger tube 87 and the mating flanges 75 and 77 bonded together to provide a completely sealed cylindrical shell unit 80. As in the previously described embodiment, the peripheral portions of the ribs 91 of the tube 87 advantageously contact both the interior wall of chamber 70 and the exterior wall of the column 90.

A plastic rod 93 or other convenient means is affixed to the opposite portions of one or both of the shell halves 71 and 73 for supporting the interior column 90 in a predetermined position.

The mating shells 71 and 73 are necked in at their bottom and top to form respective openings 95 and 97 having cylindrical flanges 99 and 101. Flange 101 snugly mates with the outside diameter of a cylindrical member 103 on the bottom and a cylindrical member 105 on the top respectively. As shown, a small annular groove 107 may be formed in each of the flanges 99 and 101 to accommodate an additional amount of bonding material for providing a hermetic seal between the blood chamber 80 and the cylinders 103 and 105.

Three dimensional, open cellular mixing material 109 is supported within cylinder 103 by a pair of annular rings 111 and 113 attached to the inner wall of cylinder 103. This mixing material completely fills the cross-sectional interior of the chamber 115 along the length of the mixing material.

An end cap 117 is secured to and closes off the bottom of cylinder 103. This cap includes one or more blood inlet ports, one such port 119 being connected to the extracorporeal blood circuit by a flexible venous blood conduit 121. In the center of the cap 117 and extending through the wall thereof is an oxygen inlet port 123 attached to a flexible oxygen line 125. The oxygen entering the inlet port 123 is caused to form a plurality of oxygen bubbles by means of a sparger 127. These bubbles flow through the venous blood entering the annular trough 129 formed by the end cap 117.

The upper cylinder 105 is secured within an opening 131 formed in a flat cover plate 133. The arterialized whole blood rises through this opening and is contained in a channel formed by the cylindrical shell 35 through which it is passed to a defoamer chamber 37 as described in the copending application of Robert M. Curtis, supra.

DETAILED DESCRIPTION OF THE EMBODIMENT OF FIGS. 5, 6 AND 7

Although the invention has been described hereinabove as integral with a blood oxygenator, the heat exchanger of this invention may be incorporated in a separate unit to be used elsewhere in extracorporeal blood circuits. Referring now to FIGS. 5, 6, and 7, the same type of helically ribbed heat transfer fluid tube 135 is mounted in a spiral configuration between an interior cylindrical column 137 and within a cylindrical chamber 139. Advantageously, peripheral portions of the ribs are in contact with the exterior of the centrally located column 137 and the interior wall of the chamber 139. As described above with reference to the embodiment of FIGS. 1 and 2, the cylinder 145 is advantageously slit along its length for facilitating insertion of the heat transfer fluid tube, after which the edges of the slit are bonded together.

Respective end caps 141 and 143 are secured at opposite ends of the cylinder 145, each with a side opening having an integral outwardly extending cylindrical bosses 147 and 149 through which passes one end of the heat exchanger tube 135. A suitable hermetic seal is formed between that portion of the exterior wall 151 of the heat transfer fluid tube 135 and the inside wall of bosses 147 and 149 to prevent any blood leakage. Typically, a suitable adhesive such as urethane glue is used to form a bond between the cylinder 145 and ends caps 141 and 143 formed of polycarbonate plastic.

The end cap members 141 and 143 each have a central aperture 153 and 155 concentric with the spirally formed heat exchanger tube 135. In each such aperture, there is mounted a port member 157 having a ridged connector portion 159 extending outwardly from the heat exchanger, four support rods 161 extending inwardly into the heat exchanger, and a through conduit 163 through which blood passes into and out of the heat exchanger. As shown in FIG. 5, the four rods 161 make contact with the peripheral end surface 167 of the centrally located column 137 to retain its end equidistant from the end caps 141 and 143.

In use, flexible water conduits 169 and 171 are attached as shown to the extending ends 173 of the ribbed heat transfer fluid tube 135, conduit 171 being connected to a suitable source of heat transfer fluid under pressure. A counterflow of blood is introduced into the heat exchanger through a flexible conduit 172 attached to the ridged connector 159. The cooled or heated blood flows out of the heat exchanger through port member 157 into flexible conduit 174 attached to the ridged connector 159.

DETAILED DESCRIPTION OF THE EMBODIMENT OF FIGS. 8, 9a and 9b

Another embodiment of a blood oxygenator incorporating an integral heat exchanger in accordance with this invention is shown in FIGS. 8, 9a and 9b. In this embodiment, the bubble oxygenator chamber 175 is formed by a cylindrical shell 177 having its lower end closed off by an end cap 179 having a side opening 181 having an integrally attached, outwardly extending cylindrical boss 183 formed in its outer wall and a necked-in portion 185 at its bottom including a cylindrical flange 187 surrounding a central aperture 189. This cylindrical flange of the end cap 179 is sized to mate with the external diameter of a cylinder 191 and bonded thereto with a suitable material such as ethylene dichloride. A three-dimensional, open cellular mixing material 193 is supported within cylinder 191 by annular rings 195 on its underside and 197 on its upper surface. As shown, material 193 completely fills the cross-sectional interior of the cylinder 191 along the length of the mixing material.

The bottom of cylinder 191 is closed off by a multiport end cap 199. In the outer wall of the end cap 199 are formed one or more blood inlet ports, one such port 201 being connected to the extracorporeal blood circuit by a flexible venous blood conduit 202. In the center of the cap 199 and extending through the wall thereof is an oxygen inlet port 203. The oxygen entering the inlet port 203 via oxygen line 205 is caused to form a plurality of oxygen bubbles by means of a sparger 207. These bubbles flow through the venous blood entering the annular trough 209 formed by the end cap 199 and the blood and oxygen mixture flow upwardly through the three-dimensional, open cellular mixing material 193 supported above the sparger 207 within the cylinder 191.

An upright column 211 is coaxially mounted within the upright cylindrical shell 177 by a horizontal rod 213 supported in appropriate semicircular slots 215 formed in the top surface of the cylinder 191. Column 211 is advantageously formed by a hollow cylindrical member 217 whose ends are sealed by circular discs 219, one of which is shown at the lower end.

The top of the cylindrical shell 177 is closed by a similar end cap 180 having a side opening 182 having an integrally attached, outwardly extending cylindrical boss 184 and a necked-in flanged portion 186 surrounding a central aperture. The inner wall of flange 186 engages the outer wall of a cylindrical member 221 which in turn is attached to a flat cover plate 223. As in the previous embodiments of FIGS. 1, 2, 3, and 4, a generally half cylindrical shell 35 is secured to the top surface of the cover plate 223 for directing the liquid blood and blood foam into a defoamer chamber 37.

The helically ribbed heat transfer fluid tube 225 is formed into a helical configuration and mounted in the space between the central column 211 and the inner wall of the cylindrical chamber 177 such that peripheral portions of the ribs 227 of the tube 225 advantageously contact or are in very close proximity to the exterior wall of the column 211 and the interior wall of the chamber 177.

The configuration of FIG. 8 is conveniently assembled by inserting the helically ribbed tube 225 along with the centrally located column 211 into the cylindrical shell 177. As described above with reference to the embodiments of FIGS. 1, 2, 5, 6, and 7, the shell 177 is advantageously slit along its length for facilitating insertion of the heat transfer fluid tube 225, after which the edges of the slit are bonded together. As shown, the respective heat exchanger tube ends will then extend above and below the shell 177. These ends are then inserted into the respective openings 181 and 182 formed in the upper and lower end caps 179 and 180.

A particular advantage of this construction is illustrated in FIGS. 9a and 9b. It has been found that after the helically formed tube 225 is inserted in the chamber 177, the tube 225, even when manufactured in conformance with the particular set of specifications, does not always ultimately provide an identical helical configuration. In particular, as noted above, there is a tendency on the part of the spirally formed tube 225 to uncoil such that it may be difficult to orient the tube ends along the parallel axes as ilustrated in FIG. 9a. In the embodiment shown, the upper and lower end caps 179 and 180 may be oriented along non-parallel axes as shown in FIG. 9b to accommodate whatever orientation the particular heat exchanger coil 225 assumes when inserted within the chamber 177.

DETAILED DESCRIPTION OF THE PREFERRED EMBODIMENT OF A PEDIATRIC BLOOD OXYGENATOR OF FIGS. 10 THROUGH 15

The preferred embodiment of a blood oxygenator incorporating an integral heat exchanger in accordance with this invention is shown in FIGS. 10 through 15. In the embodiment illustrated, a pediatric blood oxygenator comprises a bubble oxygenating chamber 240 formed by a pair of mating plastic shells, front shell 242 and rear shell 244, each including a flat peripheral flange 246 and 248 which are joined together to form a complete cylindrical shell 250. Shell halves 242 and 244 are advantageously formed by vacuum forming polycarbonate plastic, and may be advantageously bonded together with ethylene dichloride.

Rear shell half 244 includes a blood outlet opening 252 having an integral rearwardly extending, tapered neck 254, which is generally elliptical in cross section. Front shell half 242 includes an upper side opening 256 and a lower side opening 258, each having an integral forwardly extending cylindrical boss 260 through which extend the respective ends of a single helically ribbed heat transfer fluid tube 262. The inside wall of these extending cylindrical bosses 260 and the proximate exterior surface of the heat exchanger tube 262 are bonded together to effect a hermetic seal.

As with the embodiment illustrated in FIGS. 3 and 4, the preferred embodiment is advantageously assembled by inserting an extruded cylindrical interior column 264 within the helically formed ribbed tube 262. Both ends of the column 264 are hermetically sealed by end caps 265. The column 264 and the tube 262 are placed in the front shell half 242 such that the two ends of the heat exchanger tube 262 extend through the openings 256 and 258. The mating shell half 244 is placed over the heat exchanger tube 262 and the mating flanges 246 and 248 are bonded together to provide a completely sealed, cylindrical shell unit 250. The peripheral portion of the ribs 266 of the tube 262 are closely proximate to and advantageously in contact with both the interior wall of the chamber 240 and the exterior wall of the column 264.

The mating shells 242 and 244 are necked in at the bottom to form a passage 268 defined by a hollow cylindrical neck 270. The neck 270 snugly mates with the exterior wall of a hollow, injection-molded cylindrical member 272. As shown, a small, annular groove 274 may be formed in the neck 270 to accommodate additional bonding material to provide a hermetic seal between the cylindrical shell unit 250 and the member 272.

The cylindrical member 272 includes one or more blood inlet ports 276, one such port 276 being connected to the extracorporeal blood circuit by a flexible venous blood conduit (not shown).

An end cap 278 is secured to and closes off the bottom of the cylindrical member 272. In the center of the cap 278 and extending from the bottom thereof is an oxygen inlet port 280 which is attached to a flexible oxygen line (not shown). The oxygen entering the inlet port 280 is caused to form a plurality of oxygen bubbles by means of a sparger 282. These bubbles flow through the venous blood entering the cylindrical member 272. The sparger 282 fills the entire cross-section of the cylindrical member 272 and rests on an annular support 283. The sparger 282 is sealed around its periphery to the inner wall of the cylindrical member 272. Advantageously, the sparger 282 will be selected to produce small size oxygen bubbles, e.g., of the order of 0.3 cm or smaller, for most efficient oxygenation in this embodiment.

The venous blood and oxygen bubbles then rise into the oxygenating chamber 240, where they contact the exterior of the tube 262. The combination of the tube ribbing 266 and the contacting surfaces of the cylinder 264 and the chamber 240 confine the flow of blood and oxygen bubbles substantially within paths of restricted area and extended length provided by the ribbing, thus providing a tortuous path for the blood and oxygen bubbles which effect a medically adequate transfer of oxygen into the blood and removal of carbon dioxide from the blood, without additional mixing means in the oxygenator fluid path, either upstream or downstream of the ribbed tubing.

The arterialized blood, in the form of blood and blood foam, then flows out of the oxygenating chamber through the outlet opening 252 and the tapered, elliptical cross-section neck 254 into a defoamer chamber 284.

The neck 254 communicates with an opening 286 in a flat vertical plate 288 forming a side portion defoamer chamber top cap 290, which may adantageously be formed by injection-molded plastic polycarbonate. The opening 286 in turn communicates with a fluid channel member 292, located within the top cap 290, which empties the arterialized blood into an annular defoamer inlet chamber 294.

Sealingly fixed to the underside of the top cap 290 is an extruded hollow cylindrical cascade column 296 which runs through a central axial void 298 in a tubular defoamer 300. The defoamer 300 is contained within a cylindrical injection-molded, polycarbonate plastic defoamer shell 302 which is bonded hermetically around its upper periphery to a downwardly extending peripheral flange 304 depending from the top cap 290. The bottom of the defoamer shell 302 is sealed by a vacuum-formed, polycarbonate plastic bottom cap 306, which includes an inner upwardly concave portion forming an annular seat 308 for a defoamer lower support member 309. At the inner periphery of the annular seat 308, the bottom cap extends still further upwardly to form a circular, centrally raised portion 310. The support member 309 bends appropriately so as to contact the inner surface of the raised portion 310, forming a circular centrally raised platform 311, the inner surface of which closes the bottom portion of the axial void 298 and seals the bottom of the cascade column 296.

The defoamer 300 shown is essentially as described in application Ser. No. 655,039, filed Feb. 3, 1976, to Robert M. Curtis, and assigned to the same assignee as the present application. The defoamer 300 consists of an annular tube of reticulated porous sponge material, such as polyurethane foam, and is enclosed in a filter cloth 312 of nylon tricot or dacron mesh. The filter cloth 312 is secured by nylon cable ties 314 to an annular upper flange 315 which extends upwardly froam an annular defoamer upper support member 316, which, in turn, is bonded to a downwardly extending cylindrical boss 317 in the top cap 290; and a lower cylindrical flange 318 extending downardly from the defoamer lower support member 309. Both the cloth 312 and the defoamer 300 are advantageously treated with a suitable anitfoam compound.

The arterialized blood and blood foam flow from the inlet chamber 294 into the annular axial void 298 through an annular inlet 320. The majority of liquid blood entering the void 298 is guided by the column 296 to fill up the bottom of the void 298. This liquid blood flows through the defoamer 300, as generally shown by arrows 322. The blood and blodd foam enter at the upper end of the defoamer 300 so that a substantial portion of the interior wall surface of the defoamer 300 is contacted by the blood foam. As a result, a substantial portion of the defoamer 300 is used to separate the blood foam from the entrapped gas such that the foam collapses and fluid blood flows into an annular reservoir 324 between the defoamer 300 and the interior wall of the defoamer chamber 284 and settles at the bottom of the chamber 284 and in the bottom cap 306. The entrapped gas, primarily oxygen and $CO_2$, which the defoamer separates out pass out of the chamber 284 through a vent 326 located in the upper end of the chamber at the juncture of the top cap 290 and the cylindrical shell 302. As a result, only whole liquid blood collects in the reservoir 324, after having been cleansed of any particulate matter, such as blood fragments and microemboli, by the filter cloth 312. The oxygenated, filtered whole blood then passes through one or more outlet ports 328 located in the lower-most portion of the bottom cap 306 and is returned to the patient by a flexible arterial conduit (not shown).

The defoamer chamber 284 advantageously includes externally applied indicia 330 of the volume of blood contained therein. The oxygenator may also include one or more externally threaded venous blood sampling ports 332 proximate the venous blood inlet 276, and one or more arterial blood sampling ports 334 in the lower portion of the defoamer chamber 284. One or more priming ports 336 may also be provided in the top cap 290. Each of the ports 332, 334, and 336 is conveniently sealed by screw caps 338.

Figure 15:
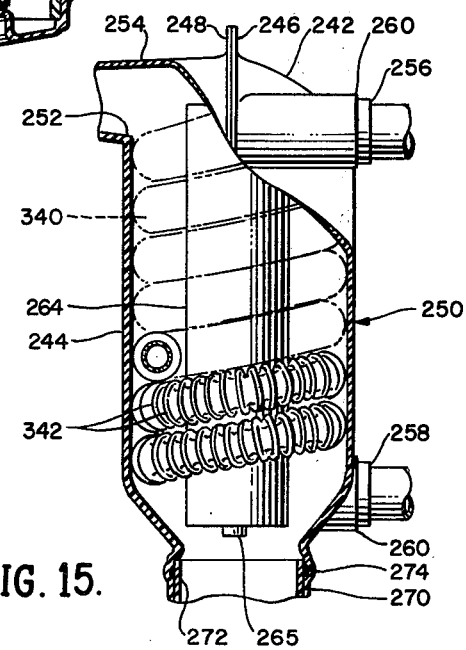
FIG. 15 is a vertical elevational partial sectional view of the oxygenating chamber of the preferred embodiment incorporating a modified form of the heat transfer fluid tube.
Figure 13:
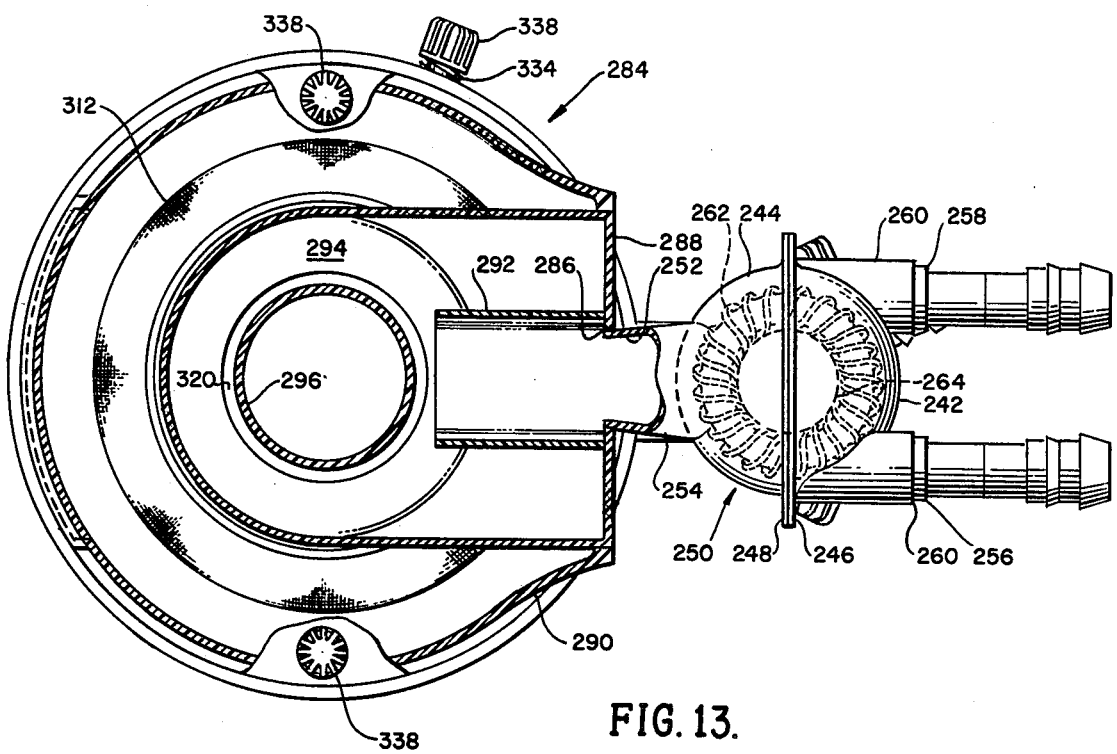
FIG. 13 is a horizontal partially sectional view taken along line 13—13 of FIG. 10.
Figure 14:
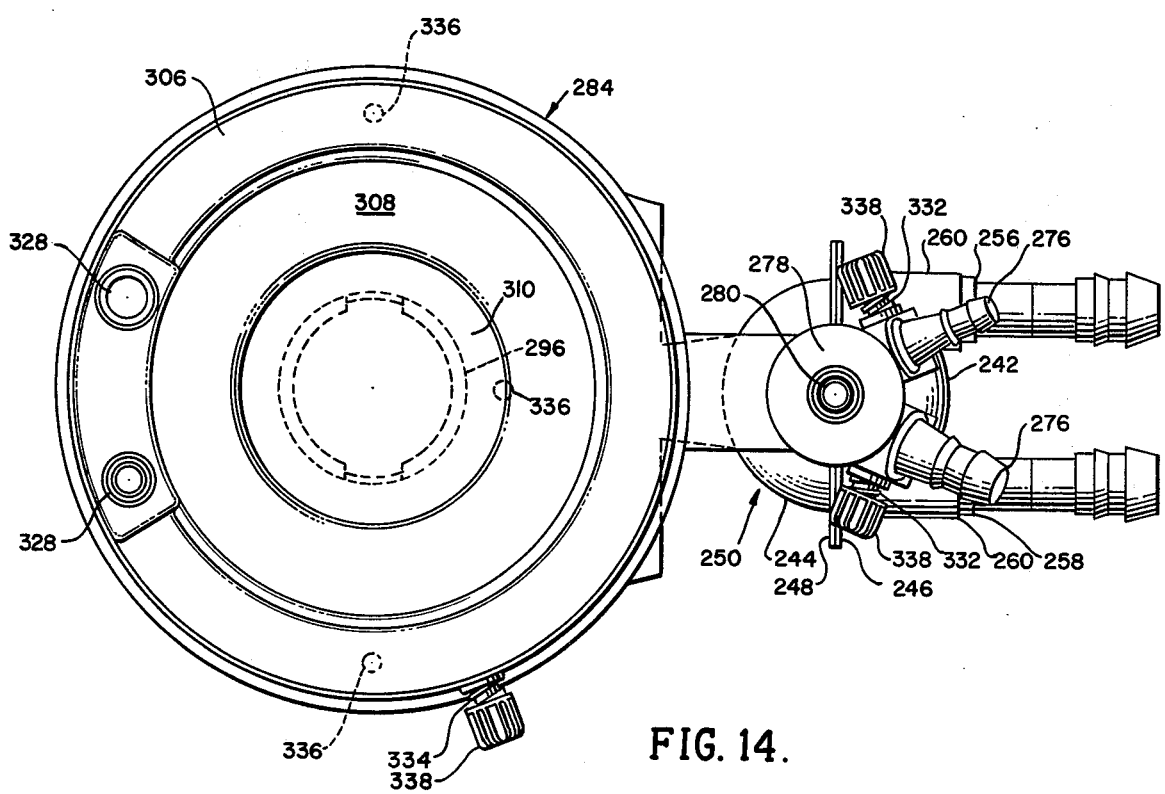
FIG. 14 is a bottom plan view taken along line 14—14 of FIG. 10, of the preferred embodiment of a blood oxygenator having an integral heat exchanger constructed in accordance with the present invention.

FIG. 15 shows a modification of the preferred embodiment wherein the helically ribbed heat transfer fluid tube is replaced by a tube 340 having discrete spaced annular hollow ribs 342 formed in the wall of the tube along its length. As with the helically ribbed tube 262 shown in FIGS. 10 through 14, the peripheral portions of the annular ribs 342 are closely proximate to and advantageously in contact with both the interior wall of the chamber 240 and the exterior wall of the column 264. These discrete spaced annular ribs provide a plurality of discontinuous flute passages around the tube which, when their individual lengths are added, total a distance considerably longer than the length of the fluid conduit. The combination of the ribs 342 and the contacting surfaces of the column 264 and the chamber 240 confine the flow of blood and oxygen bubbles substantially within extended length, restricted area paths and provide a thorough mixing of the blood and oxygen bubbles, thereby effecting a medically adequate transfer of oxygen into the blood and $CO_2$ from the blood without additional mixing means. Except for the configuration of the ribbing on the tube, the embodiment illustrated in FIG. 15 is in all other respects identical to that illustrated in FIGS. 10 through 14.

The helically-ribbed heat transfer fluid tube 262, shown in FIGS. 10 through 14, is advantageously formed of a continuous length of aluminum tubing with the exterior coated with a polyurethane coating, as discussed above or, alternatively, the the exterior surfaces are electrolytically oxidized, or anodized, to form a "hard anodized" coating, as disclosed and claimed in applicant's copending application Ser. No. 863,988 filed 12/23/77.

The annular-ribbed heat transfer fluid tube 340, shown in FIG. 15, may likewise be formed of anodized or polyurethane coated aluminum. Alternatively, it may be formed of brass or bronze tubing having a blood compatible coating.

The preferred embodiment of FIGS. 10 through 15 is suited for use in both adult and pediatric applications. It is advantageous to construct the oxygenating chamber with as small a volume as possible, consistent with the requirements for heat and gas transfer so as to minimize the amount of blood contained in the oxygenating chamber during use.

By way of specific example, a pediatric oxygenator with an integral heat exchanger constructed in accordance with the preferred embodiment comprises an oxygenating chamber 240 having an inside diameter of approximately two inches, and contains a central cylindrical column 264 having an outside diameter of approximately one inch. The heat exchanger tube 261 is formed of half-inch outside diameter aluminum tubing, which, when twisted to form the helical ribbing, has an outside diameter of 0.490 inches from ridge of the ribs and 0.340 inches from groove to groove between the ribs. The wall thickness of the tube 262 is approximately 0.014 inches. The tubing is anodized, as hereinabove described, and the anodized coating adds approximately 0.001 inches to the wall thickness and approximately 0.002 inches to the respective outside diameter measurements. When completely assembled, and incorporating the heat exchanger tube 262 and the central column 264, the oxygenating chamber has a capacity of approximately 100 milliliters. The adult sized unit is larger in scale with a capacity of approximately 450 milliliters.

In constructing the oxygenating chamber, it is necessary to coil the tube 262 tightly so as to have the peripheral portions of the ribbing come into contact with, or at least be closely proximate to, the exterior surface of the central column 264. The hollow ribbing on the tube enables the tube to be so coiled without kinking. Any kinking would be quite deleterious since it would result in obstructed fluid flow and also a weakened wall structure, which would make the tube prone to leaks. This ability to be tightly coiled displayed by the ribbed tubing makes possible an oxygenating chamber having the relatively small capacity of 100 milliliters, and such a capacity has been found to be particularly advantageous in pediatric applications.

Tests conducted on both adult and pediatric units constructed in accordance with this embodiment show a medically adequate transfer of oxygen into the blood sand removal of carbon dioxide therefrom. In general, tests conducted on identical units with and without the mixing material of the prior embodiments show that to achieve a given level of oxygenation compared to these previous described embodiments, a higher level of oxygen flow rate is required for a given blood flow rate. In addition these tests show that the level of oxygenation increases with an increase of the blood flow rate, e.g., at a blood flow of 6 liters per minute, the oxygen gas content of the arterialzied blood output from the embodiment of FIGS. 10-14 with a 1:1 oxygen to blood ratio closely approaches the oxygen gas content achieved with the prior embodiments, whereas at a blood flow rate of 2 liters per minute, a ratio of greater than 1:1 is required to achieve oxygen gas content levels which are comparable to those achieved with the prior embodiments of FIGS. 1, 2, 3, 4, 8 and 9.

By way of specific example, the gas transfer data obtained during a specific test are listed in Table 1. This test was conducted Nov. 1, 1977, on a female Suffolk lamb weighing 26 kg which underwent a six-hour, partial veno-arterial cardiopulmonary bypass using the oxygenator of the preferred embodiment. The data indicate efficient oxygenation with $CO_2$ removal in an oxygenator having an integral heat exchanger constructed in accordance with the present invention, and lacking any additional mixing structure in the oxygenating chamber. The oxygenator used in these tests used a heat exchanger of anoidzed aluminum as previously described.

TABLE I

| Venous Parameters | | | | | | O$_2$ Transfer Volume | CO$_2$ Transfer Volume | |
|---|---|---|---|---|---|---|---|---|
| O$_2$ Saturation (%) | pH | P-CO$_2$ (torr) | Hemoglobin (gmHb/ 100 ml blood) | V:Q (Oxygen Flow) (Blood Flow) | Q (blood flow) (l/min) | ΔO$_2$ Content (mlO$_2$/ 100 ml blood) | ΔCO$_2$ Content (mlCO$_2$/ 100 ml blood) | ΔP-O$_2$ (torr) |
| 71.6 | 7.58 | 32 | 9.8  | .37 | 1.5 | 3.41 | 1.85 | 90 |
| 67.6 | 7.50 | 38 | 10.3 | .37 | 1.5 | 3.96 | 2.34 | 64 |
| 62.1 | 7.46 | 48 | 10.3 | .37 | 1.5 | 4.55 | NRV[1] | 52 |
| 56.5 | 7.46 | 43 | 8.8  | .50 | 1.5 | 5.10 | NRV[1] | 86 |
| 52.1 | 7.43 | 43 | 9.1  | .50 | 1.5 | 5.21 | 2.38 | 45 |
| 48.1 | 7.49 | 41 | 8.7  | 1.0 | 1.5 | 5.89 | 4.76 | 171 |
| 40.7 | 7.47 | 43 | 8.8  | 1.0 | 0.5 | 6.82 | 4.91 | 178 |
| 66.6 | 7.49 | 41 | 9.1  | .68 | 2.2 | 4.05 | 3.72 | 280 |
| 65.5 | 7.48 | 43 | 9.5  | .30 | 2.2 | 4.03 | 1.35 | 93 |

[1] No recorded vent gas (recording equipment failure).

A number of factors contribute to the excellent heat transfer efficiency of the present invention and include the following:

1. The combination of the flutes of the heat transfer fluid tube and proximate inner and outer surface walls of the blood chamber provides a plurality of continuous, restricted area flow paths offering substantially uniform flow impedance to the blood and blood foam. As a result, the blood and blood foam have a long residence time in the heat exchanger. Moreover, this structure avoids areas of stagnation which otherwise hinder heat transfer from the blood and are alos undesirable from a physiological standpoint. In the tests conducted to date on the embodiments of FIGS. 3, 4, 8, 9 and 10 through 14, the blood and blood foam was observed to be in constant circulation through these restricted flow paths and having extensive contact with and long residence time with the heat exchanger tube. Only minimal areas of stagnation were evident.

2. The extensive hollow ribs of the heat transfer fluid tube provide a substantial surface area of transferring heat from the heat transfer fluid to the blood and blood foam. The tubes used in the above-described embodiments typically have an external surface area of the order of 200 to 300 square inches. The surface area of the tubes in pediatric unit is on the order of 100 square inches.

3. Although the direction of fluid flow through the heat exchanger tube may be in either direction, the heat transfer performance is optimized by operating as a counterflow exchanger, i.e., in the manner described above wherein the blood and heat transfer fluid flow in generally opposite directions.

4. The wall thickness of the ribbed tube may be relatively thin, e.g., 0.014 to 0.016 inch, so as to further improve its heat transfer properties. As disclosed and claimed in the copending application Ser. No. 863,988, supra, very high thermal conductivity is achieved using an anodized aluminum tube. The polyurethane coated aluminum tubes described herein also have a high thermal conductivity, notwithstanding that the polyurethane coating reduces the overall thermal conductivity of the aluminum tube by some 15 percent.

5. The ribbed heat exchanger tube has a sufficiently large average internal diameter, e.g., approximately 0.5 inch, for providing a high rate of flow of the heat transfer fluid, e.g., 21 liters/minute of water. The average inside diameter of the tubes used in pediatric units is approximately 0.34 inch and accommodates a proportionately lower flow rate.

Although the integral heat exchanger embodiments described above have incorporated the heat exchanger within the oxygenation chamber, it will be apparent to those knowledgeable in the art that the significant features of the heat exchanger tube which contribute to its high heat transfer efficiency will be beneficial in other locations within the blood oxygenator. Thus, by way of specific example, the ribbed heat transfer fluid tube may be located within the defoamer column such that the blood flowing within or through the defoamer member is caused to circulate through the flutes of the heat exchanger tube.

The integral nature of the heat exchanger tube also provides an important advantage in providing an effective seal for preventing any possible contamination of the blood by the heat transfer fluid. Thus, in the present invention, the heat exchanger tube is advantageously constructed as a continuous member with no connections being made to the tube within the blood chamber. Any leak at the connection of the heat exchanger tube and the flexible wateer or other heat transfer fluid conduit will merely leak water or other fluid external of the blood chamber.

In addition, the thickness of the heat exchanger tube, after being formed into a ribbed configuration, is ample to handle fluid pressures considerably higher than those encountered in clinical practice. This is important since typically the heat exchanger tube is connected directly to a water faucet in the operating room which, turned full on, may deliver water at a pressure as high as 60 psi. Inadvertent closing of the drain discharge can then build up pressure within the heat exchanger to 60 psi. Such high pressures can rupture certain prior art heat exchanger configurations concurrently in extensive use in extracorporeal blood circuits. In contrast, in the present invention, the ribbed tubes have been tested at substantially high pressures, i.e., 120 psi without any indication of structural damage or rupture.

In addition to its excellent heat transfer characteristics, the present invention is efficiently and economically manufactured. Thus, the ribbed tube is an integral unit which may be completely tested for leaks before and/or after assembly into the blood carrying chamber. Also, it has been found that pin hole or other small leaks in the aluminum heat exchanger tube are sealed by the polyurethane coating. Advantageously, the coating covers the entire tube including those portions extending through the sealed openings of the blood chamber so as to provide this additional protection against leakage.

What is claimed is:

1. A method for regulating the temperature of venous blood in an extracorporeal blood circuit and simultaneously oxygenating said venous blood comprising the steps of:

introducing said venous blood and oxygen bubbles into a chamber;

oxygenating said venous blood by flowing the blood and said oxygen bubbles over the exterior surface of a conduit in said chamber, said conduit having an integral hollow rib means along its length providing a flute passage means whose total length is considerably longer than the length of said conduit; and regulating the temperature of said blood by flowing heat transfer fluid of a predetermined temperature through the interior of said conduit and hollow rib means during said oxygenating step.

2. A method for regulating the temperature of venous blood in an extracorporeal circuit and simultaneously oxygenating said venous blood comprising the steps of:

introducing said venous blood and oxygen bubbles into a chamber;

oxygenating said venous blood by flowing the blood and said oxygen bubbles through paths of restricted area and extended length provided by a flute means formed by an integral hollow rib means along the length of a tube in said chamber; and regulating the temperature of said blood by flowing heat transfer fluid of predetermined temperature through the interior of said tube and said hollow rib means during said oxygenating step.

3. A method for regulating the temperature of venous blood in an extracorporeal blood circuit and simultaneously oxygenating said venous blood comprising the steps of:

oxygenating said blood by flowing the blood and oxygen bubbles through a plurality of paths of restricted area and extended length provided by a flute means formed by (i) an integral, hollow rib along the length of a tube and (ii) a wall of a chamber connected in said extracorporeal blood circuit which is in contact with or located proximate to peripheral portions of said rib; and simultaneously regulating the temperature of said blood by flowing heat transfer fluid of predetermined temperature through the interior of said tube and hollow rib during said oxygenating step.

4. A blood oxygenator having an integral heat exchanger for regulating the temperature of the blood flowing in an extracorporeal blood circuit comprising:

an oxygenating chamber;

first means for introducing blood and bubbles of oxygen into said oxygenating chamber for forming blood foam within said chamber; and second means for both (a) oxygenating the blood flowing in said blood circuit by transferring oxygen into the blood and removing carbon dioxide from the blood and (b) simultaneously regulating the temperature of said blood, said second means comprising a heat transfer fluid conduit including heat exchange fluid inlet and outlet means and having rib means along its length, said rib means being located in contact with or closely proximate to the inner wall of said oxygenating chamber so that substantially all of said blood and blood foam produced by said first means flows in contact with external surfaces of said heat transfer fluid conduit through a plurality of restricted area, extended length flow paths around the exterior of the heat transfer fluid conduit provided by said rib means in combination with said inner wall prior to any substantial defoaming of the blood foam and with minimal areas of stagnation for said blood and blood foam with a resulting relatively long residence time po the bloodand blood foam in contact with said heat transfer fluid conduit.

5. The blood oxygenator having an integral heat exchange of claim 4, wherein said rib means provide a a flute passage means whose total length is considerably longer than the length of said cobduit.

6. The blood oxygenator having an integral heat exchanger of claim 5 wherein said continuous helical flute passage is considerably longer than the length of said fluid conduit.

7. The blood oxygenator having an integral heat exchanger of claim 4 wherein said rib means is a plurality of discrete hollow annular ribs disposed along the length of said heat transfer fluid conduit.

8. The blood oxygenator having an integral heat exchanger of claim 7 wherein said annular ribs provide aplurality of annular flute passages around the tube which total a distance considerably longer than the length of the fluid conduit.

9. The blood oxygenator having an integral heat exchanger of claim 4, wherein said second means effects substantially all of the transfer of oxygen into the blood and the removal of carbon dioxide from the blood while said blood and blood foam are in contact with second means.

10. The blood oxygenator having an integral heat exchanger of claim 9 wherein said chamber has first and second sealed openings through which extend the opposite ends ofsaid heat transfer fluid conduit whereby connections to said heat exchange fluid inlet and outlet means are made outside said chamber.

11. The blood oxygenator having an integral heat exchanger of claim 9 wherein the flow of heat transfer fluid through said heat transfer fluid conduit is substantially opposite the direction of the flow of said blood to provide a counterflow operation.

12. The blood oxygenator having an integral heat exchanger of claim 9 wherein said heat transfer fluid conduit has three substantially equally spaced, substantially continuous hollow helical ribs along its length in a triple helix configuration providing plural of said continuous helical flute passages considerably longer than the length of said fluid conduit.

13. The blood oxygenator having an integral heat exchanger of claim 9 wherein said heat transfer fluid conduit is a continuous length of metal tubing having said rib means formed integrally therein.

14. The blood oxygenator having an integral heat exchanger of claim 9 wherein said heat transfer fluid conduit has an overall helical configuration.

15. The blood oxygenator having an integral heat exchanger of claim 14 wherein a centrally located cylindrical column is located within said chamber and said helically configured heat transfer fluid conduit is located between said column and the interior wall of said chamber so that said exterior wall of said column is located in contact with or closely proximate to peripheral portions of said rib means.

16. The blood oxygenator having an integral heat exchanger of claim 9 wherein said chamber comprises two halves mated along a seam, said halves being located over and surrounding said heat transfer fluid conduit and bonded together to form a hermetic seal along said seam.

17. The blood oxygenator having an integral heat exchanger of claim 12 wherein one of said chamber halves includes first and second openings through which extend the opposite ends of said heat transfer fluid conduit.

18. A blood oxygenator having an integral heat exchanger comprising:
an oxygenating chamber;
first means for introducing venous blood and bubbles of oxygen into said oxygenator chamber for forming blood foam; and
second means for (a) oxygenating said venous blood by transfering oxygen into the venous blood and removing carbon dioxide from the venous blood and (b) simultaneously regulating the temperature of said venous blood, said second means comprising:
a heat transfer tube including heat exchange fluid inlet and outlet means and having integral rib means along its length for providing a flute passage means whose total length is considerably longer than the length of said tube, said tube having an overall helical configuration with peripheral portions of said rib means in contact with or closely proximate to a wall of said oxygenating chamber so that substantially all of said venous blood and blood foam flows in contact with external surfaces of said heat transfer tube through a plurality of flow paths of restricted area and extended length around the exterior of said tube prior to any substantial defoaming of the blood foam, said flow paths being with minimal areas of stagnation for said venous blood and blood foam and formed by said flute passage in combination with a wall of said oxygenating chamber for achieving long residence time of the blood and blood foam in contact with said heat transfer tube.

19. The blood oxygenator having an integral heat exchanger of claim 18, wherein said rib means is a plurality of discrete hollow annular ribs disposed along the length of said heat transfer fluid conduit.

20. The blood oxygenator having an integral heat exchanger of claim 18 wherein said second means effects substantially all of the transfer of oxygen into the blood and the removal of carbon dioxide from the blood while said blood and blood foam are in contact with said second means.

21. The blood oxygenator of claim 20 wherein a centrally located column is located in a chamber of said oxygenator and said heat transfer tube is formed in a helical configuration located in the space between the exterior wall of said column and the interior wall of said chamber so that peripheral portions of said rib means are in contact with or closely proximate to the exterior wall of said column and the interior wall of said chamber.

22. The oxygenator of claim 20 wherein said oxygenating chamber comprises two halves mated along a seam, one of said halves having first and second sealed openings through which extend the opposite ends of said heat transfer fluid conduit.

23. A blood oxygenator having an integral heat exchanger for regulating the temperature of the blood flowing in an extracorporeal blood circuit comprising:
an oxygenating chamber;
first means for introducing blood and bubbles of oxygen into said oxygenating chamber; and
second means for both (a) effecting substantially all of the transfer of oxygen into the blood and the removal of carbon dioxide from the blood and (b) simultaneously regulating the temperature of said blood, said second means comprising:
a heat transfer fluid conduit including heat exchange fluid inlet and outlet means and having a substantially continuous hollow helical rib along its length providing a continuous helical flute passage considerably longer than the length of said fluid conduit, said helical rib being located in contact with or closely proximate to wall means of said blood oxygenator so that substantially all of said blood and blood foam produced by said first means flows in contact with external surfaces of said heat transfer fluid conduit through a plurality of restricted area, extended length flow paths around the exterior of the heat transfer fluid conduit provided by said helical flute passage in combination with said wall means prior to any substantial defoaming of the blood foam with a resulting relatively long residence time of the blood and blood foam in contact with said heat transfer fluid conduit.

24. A blood oxygenator having an integral heat exchanger for regulating the temperature of the blood flowing in an extracorporeal blood circuit comprising:
an oxygenating chamber;
first means for introducing blood and bubbles of oxygen into said oxygenating chamber;
second means for both (a) effecting substantially all of the transfer of oxygen into the blood and the removal of carbon dioxide from the blood and (b) simultaneously regulating the temperature of said blood, said second means comprising:
heat transfer means having a plurality of annular ribs along its length providing a blood flow passage considerably longer than the length of said heat transfer means, said ribs being located in contact with or closely proximate to wall means of said blood oxygenator so that substantially all of said blood and blood foam produced by said first means flows in contact with external surfaces of said heat transfer means through a plurality of restricted area, extended length flow paths around the exterior of the heat transfer means provided by said blood flow passage in combination with said wall means prior to any substantial defoaming of the blood foam with a resulting relatively long residence time of the blood and blood foam in contact with said heat transfer means; and
third means coupled to said heat transfer means for supplying or removing heat energy from said heat transfer means.

* * * * *